(12) United States Patent
Cho et al.

(10) Patent No.: US 12,036,397 B2
(45) Date of Patent: Jul. 16, 2024

(54) LUER-LOCK FASTENING NEEDLE HUB

(71) Applicant: PoongLim Pharmatech Inc., Gunsan (KR)

(72) Inventors: Hee Min Cho, Gunsan (KR); Mi Heui Cho, Gunsan (KR); Jong Deok Yun, Gunsan (KR); Jae Cheon Kim, Jeonju (KR)

(*) Notice: Subject to any disclaimer, the term of this patent is extended or adjusted under 35 U.S.C. 154(b) by 0 days.

(21) Appl. No.: 17/193,167

(22) Filed: Mar. 5, 2021

(65) Prior Publication Data
US 2022/0226585 A1    Jul. 21, 2022

(30) Foreign Application Priority Data
Jan. 18, 2021  (KR) .................. 10-2021-0007104

(51) Int. Cl.
    *A61M 5/34*    (2006.01)
    *A61M 5/31*    (2006.01)
    *A61M 5/315*   (2006.01)
    *A61M 5/32*    (2006.01)

(52) U.S. Cl.
    CPC .......... *A61M 5/347* (2013.01); *A61M 5/3137* (2013.01); *A61M 5/31511* (2013.01); *A61M 5/3202* (2013.01); *A61M 5/3293* (2013.01); *A61M 2005/31516* (2013.01)

(58) Field of Classification Search
    CPC .............. A61M 5/347; A61M 5/3137; A61M 5/31511; A61M 5/3202; A61M 5/3293; A61M 2005/31516; A61M 2005/31523
    See application file for complete search history.

(56) References Cited

U.S. PATENT DOCUMENTS

| | | | | |
|---|---|---|---|---|
| 5,782,803 A | * | 7/1998 | Jentzen | ......... A61M 5/347 604/218 |
| 9,913,949 B2 | | 3/2018 | de Beer | |
| 2004/0153038 A1 | * | 8/2004 | Guala | ......... A61M 5/3202 604/263 |

FOREIGN PATENT DOCUMENTS

KR   20-0467647 Y1   6/2013

* cited by examiner

*Primary Examiner* — James D Ponton
*Assistant Examiner* — Hong-Van N Trinh
(74) *Attorney, Agent, or Firm* — KORUS Patent, LLC; Seong IL Jeong

(57) ABSTRACT

A Luer-lock fastening needle hub is proposed. The Luer-lock fastening needle hub has an insertion groove for a front end of a tapered tube of a barrel to receive the tapered tube into which a plunger is inserted, so that a plunger contact surface is inserted into the tapered tube of a front discharge end of the barrel. The Luer-lock fastening needle hub has a needle cap fastening grooves formed along an outer circumference thereof and "V"-shaped insertion guides are formed in four direction at front portions of openings of the needle cap fastening grooves, so that fastening protrusions formed on an inner surface of a needle cap are unaffectedly guided by the "V"-shaped insertion guides and are easily aligned and fastened to the needle cap fastening grooves.

1 Claim, 5 Drawing Sheets

LUER-LOCK FASTENING NEEDLE HUB

CROSS REFERENCE TO RELATED APPLICATION

The present application claims priority to Korean Patent Application No. 10-2021-0007104, filed Jan. 18, 2021, the entire contents of which is incorporated herein for all purposes by this reference.

BACKGROUND OF THE INVENTION

Field of the Invention

The present disclosure relates generally to a Luer-lock fastening needle hub and, more particularly, to a Luer-lock fastening needle hub in which a structure is improved to be capable of injecting the entire amount of injection liquid without injection liquid remaining at the injection completion time during the injection to a patient with a syringe, and to be capable of allowing easy fastening of a needle cap.

Description of the Related Art

In general, syringes are classified into a general type syringe and a Luer-lock type syringe. The general type syringe includes a barrel as a main body of a syringe, a push rod with a finger grip, a plunger fastened to a front end of the push rod and pushing injection liquid in a piston manner, and an injection needle fastened to a tapered tube at a front end of the barrel, and the Luer-lock type syringe has a structure in which a separate Luer-lock connector is provided to be screwed to the front end of the barrel and a hub to which the injection needle is mounted is screwed to the Luer-lock connector.

In the syringe configured as described above, the plunger made of rubber or silicone is mounted by being fitted over an end of the push rod. In general, the shape of a front end of the plunger is formed in a horizontal surface or a slight conical shape, so injection liquid remaining in the tapered tube formed at an end of the barrel cannot be discharged from the syringe and is disposed of while remaining in the syringe. When the plunger reaches the front end of the barrel, the injection liquid should pass through an inner diameter of the injection needle, which is relatively smaller than a diameter of the barrel, so that the plunger is subjected to an increasingly larger reaction pressure due to the bottleneck state. Therefore, it is difficult for medical staff to push injection liquid to the end of the barrel, when multiple injections are required, the medial staff becomes fatigued, and when a viscous injection liquid is injected, it takes more hand force to push the injection liquid, so female nurses with weak finger grips have difficulty and patients feel pain.

As an example, Korean Utility Model Registration No. 20-0467647 "Syringe" was disclosed. In the syringe of the related art, two pistons are provided as plungers and a partition piston is inserted at a distance from a main piston fastened to a piston rod. When different injection liquids are filled at a distance from each other and the piston rod is pressed, the partition piston is pressed and moved together with the main piston pressed, injection liquid filled in a front portion of the barrel is moved and mixed with injection liquid in a rear portion thereof through a moving portion, and the mixed injection liquid is moved and pressed toward a plug at a front end of the barrel and is injected by being discharged through the injection needle.

However, the syringe of the related art is also configured such that the front end of the piston that is provided as a plunger is formed in a plane with no different from conventional syringes. Therefore, when injection liquid is moved toward the front plug of the barrel, reaction pressure is applied even stronger, and two pistons require more pressure, so it is difficult for nurses having weak hand force to use the syringe.

As another example, U.S. Pat. No. 9,913,949 B2 is disclosed. In the related art, a syringe is a Luer-lock type, and has a plunger formed in a long shape to be fitted into a syringe connector of a front end extension portion of a syringe barrel. On a front end of the plunger, a conical center protrusion is formed at a needle receiving portion of a syringe hub, so that the injection is performed while reaction pressure applied to the plunger is reduced when a front end surface of the plunger is coupled to the syringe hub.

However, the Luer-lock type syringe hub is configured such that the front end surface of the plunger is formed in a plane and the conical protrusion is formed at the center of the syringe hub to be brought into close contact with the front end horizontal surface of the plunger. Therefore, a space is generated by a height of the conical protrusion and injection liquid remaining in the space is discarded in a remaining state.

DOCUMENTS OF RELATED ART (Patent Document 1) Korean Utility Model Registration No. 20-0467647 (Jun. 19, 2013); and
(Patent Document 2) U.S. Pat. No. 9,913,949 B2 (Mar. 13, 2018)

SUMMARY OF THE INVENTION

Accordingly, the present disclosure has been made keeping in mind the above problems occurring in the related art, and the present disclosure is intended to propose a Luer-lock fastening needle hub. In the Luer-lock fastening needle hub, an insertion groove is formed to correspond to a front end of a tapered tube of a front discharge end of a barrel, so that a center portion of the needle hub is unaffectedly inserted into the front end of the tapered tube of the barrel, and the needle hub and the plunger, which has a three-step structure in which a diameter thereof is gradually reduced as the plunger goes frontward, are brought into close contact with each other without clearance to prevent the remaining injection liquid in the barrel. In addition, in the Luer-lock fastening needle hub, needle cap fastening grooves are formed along an outer circumference of the needle hub and "V"-shaped insertion guides are formed in four directions at front portions of openings of the needle cap fastening grooves, so that fastening protrusions formed on an inner surface of a needle cap are unaffectedly guided by the "V"-shaped insertion guides and are easily aligned and fastened to the needle cap fastening grooves.

In order to achieve the above objective, according to one aspect of the present disclosure, there is provided a Luer-lock fastening needle hub. A plunger applied to the present disclosure may be formed in a long conical shape and have a three-step structure in which a diameter thereof may be gradually narrowed and intervals between steps may be gradually shortened as the plunger goes toward an end thereof, and corresponding to the structure of the plunger, a tapered tube, which may receive the plunger, of a front discharge end of a barrel may have three-step grooves in which an inner diameter thereof may be gradually narrowed and intervals between the grooves may be gradually shortened as the tapered tube goes frontward, and the steps of the plunger may be coupled to the grooves in the tapered tube, so that reaction pressure further applied to the plunger as the plunger goes to the end of the discharge may be distributed to perform an injection without excessive effort. In order to insert the tapered tube of the front discharge end of the barrel to which the plunger is inserted, a insertion groove for the tapered tube of the barrel may be formed on an inside of the needle hub, so that a plunger contact surface may be inserted into the tapered tube of the front discharge end of the barrel. Needle cap fastening grooves may be formed along an outer circumference of the needle hub, and "V"-shaped insertion guides may be formed in four directions at the front portions of the openings of the needle cap fastening grooves, so that fastening protrusions formed on an inner surface of a needle cap may be unaffectedly guided by the insertion guides and easily aligned and fastened to the needle cap fastening grooves.

According to the present disclosure, the needle hub is configured to have the insertion groove for the tapered tube of the barrel to allow the tapered tube of the front discharge end of the barrel to be inserted into the insertion groove, so that the plunger contact surface is unaffectedly inserted into the tapered tube of the front discharge end of the barrel. Accordingly, the injection is performed while the front end of the plunger and the needle hub are in close contact with each other. The plunger applied to the present disclosure is formed in a long conical shape, and has the three-step structure in which a diameter thereof is gradually reduced and intervals between the steps are gradually shortened as the plunger goes frontward. Corresponding to the structure of the plunger, the inside of the tapered tube of the front discharge end of the barrel into which the plunger is inserted has the three-step structure in which a diameter is gradually reduced and intervals between the steps are gradually shortened as the tapered tube goes frontward. Therefore, the reaction pressure, which is further applied when the injection liquid reaches an end point of the discharge after the plunger is inserted into the tapered tube, is sequentially distributed, and the injection can be performed without excessive effort. In addition, when the front end of the plunger and the plunger contact surface in the needle hub are brought into close contact with each other, the contact can be performed without the reaction pressure applied to the plunger and the injection can be performed without the remaining injection liquid in the syringe. Furthermore, the needle cap fastening grooves are formed along the outer circumference of the needle hub and the "V"-shaped insertion guides are formed in four directions at the front portions of the openings of the needle cap fastening grooves, so that the fastening protrusions formed on the inner surface of the needle cap can be guided by the "V"-shaped insertion guides and can be easily aligned and fastened to the needle cap fastening grooves.

BRIEF DESCRIPTION OF THE DRAWINGS

The above and other objectives, features, and other advantages of the present disclosure will be more clearly understood from the following detailed description when taken in conjunction with the accompanying drawings, in which.

DETAILED DESCRIPTION OF THE INVENTION

Figure 1:
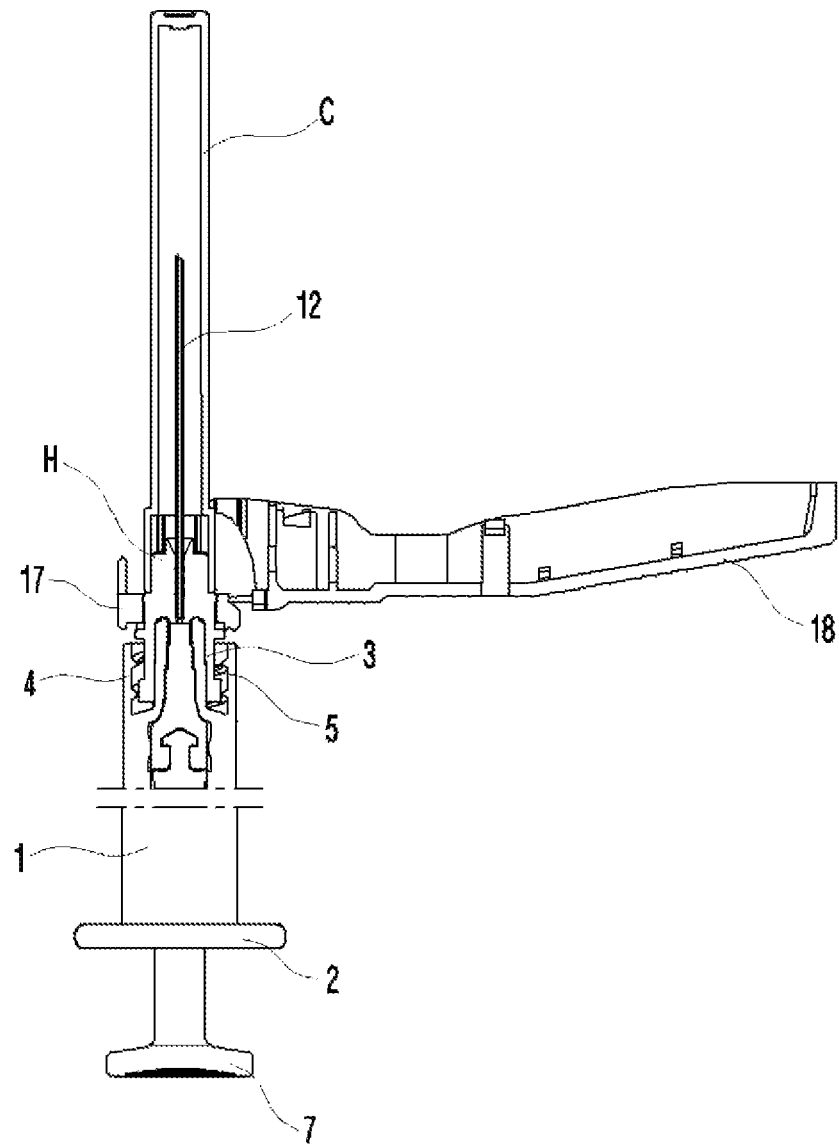
FIG. 1 is a partially cutaway side view showing a fastened state of a syringe having a reuse prevention structure according to the present disclosure.
Figure 2:
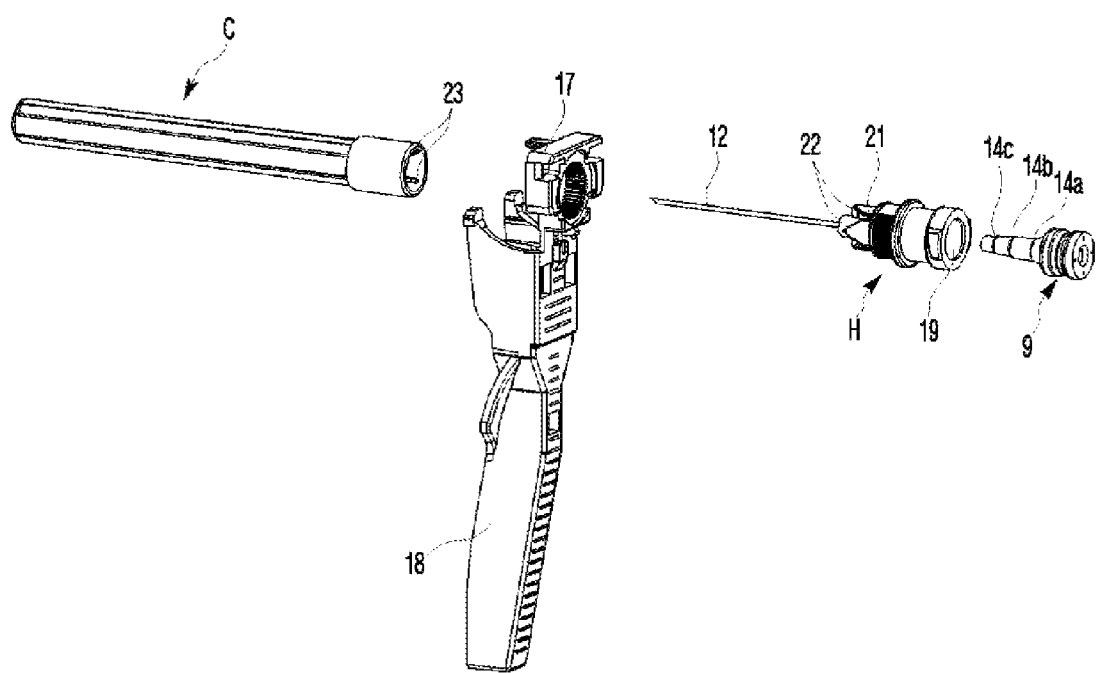
FIG. 2 is disassembled perspective view showing the syringe having the reuse prevention structure according to the present disclosure.
Figure 3:
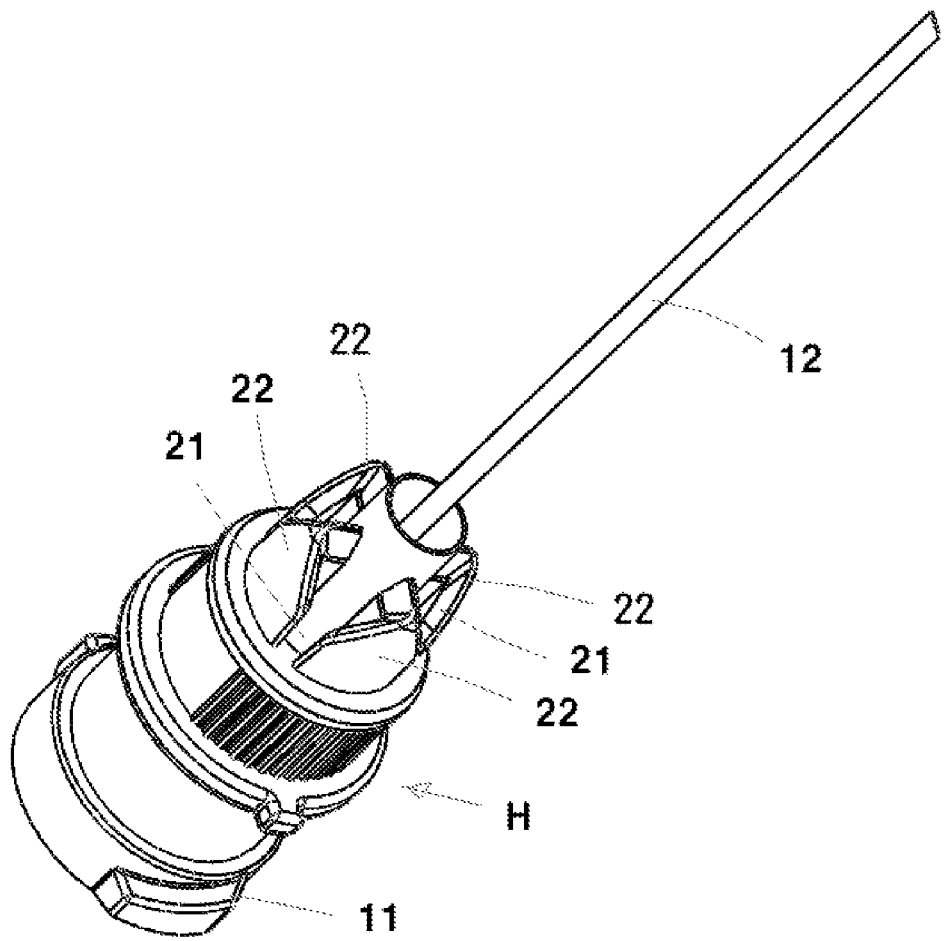
FIG. 3 is a perspective view showing a Luer-lock fastening needle hub according to the present disclosure.
Figure 4:
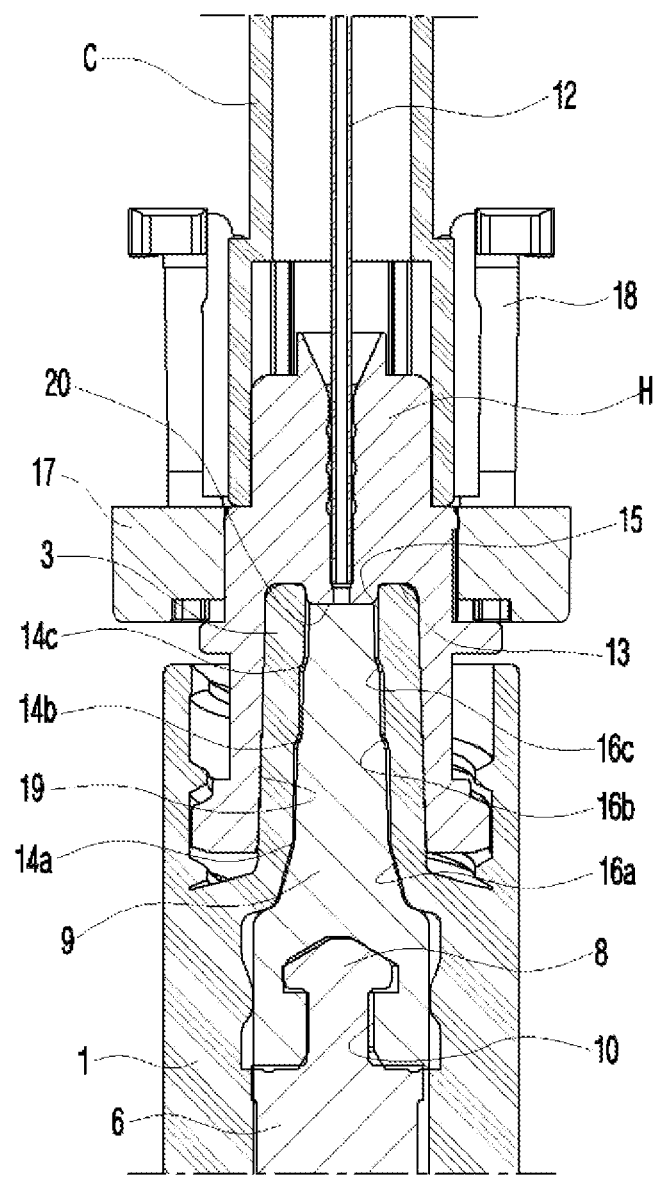
FIG. 4 is an enlarged sectional view showing a main part of the assembled syringe having the reuse prevention structure according to an embodiment of the present disclosure.

The above and other objectives, features, and advantages of the present disclosure will be more clearly understood from the following detailed description taken in conjunction with the accompanying drawings.

In the flowing description, unless otherwise defined, all terms including technical and scientific terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Hereinbelow, a Luer-lock fastening needle hub according to an exemplary embodiment of the present disclosure will be described in detail with reference to accompanying drawings.

As shown in the drawings, a Luer-lock fastening needle hub H constitutes a Luer-lock fastening type syringe having a reuse prevention structure. A barrel 1 has a finger grip 2 at a rear end thereof and a Luer-lock connector 4 in which a thread portion 5 is formed an inner surface outside a tapered tube 3 of a front discharge end thereof, and a plunger rod 6 having a push end 7 at a rear end thereof is inserted into the barrel 1. Whereby, a plunger fastening protrusion 8 at a front end of the plunger rod 6 is fitted into a plunger fastening closed hole 10 formed inside a rear end of a plunger 9 to couple the plunger rod 6 to the plunger 9.

Meanwhile, fastening protrusion steps 11, which are formed by protruding on an opposite sides of a rear ends of the needle hub H to correspond to the thread portion 5 of the Luer-lock connector 4 formed on the front end of the barrel 1, passes through and joins to the thread portion 5, so that the needle hub H is fastened to the barrel 1. An injection needle 12 is fastened to a front end of the needle hub H by passing through an inside of the needle hub H. An insertion groove 13 for the tapered tube of the barrel is formed in of a rear portion of the needle hub H. The tapered tube 3 of the barrel 1 is inserted into the insertion groove 13 with the screwing and Luer-lock fastening of the needle hub H, so that the needle hub H to which the injection needle 12 is mounted and the barrel 1 are fastened to each other. In configuring the plunger 9, the plunger 9 is formed in a tapered long conical shape made of rubber or silicone, the plunger 9 consists of a three-step structure in which an outer diameter of the plunger 9 is gradually reduced and an interval between the steps is shortened as the plunger 9 goes frontward to a first step 14*a*, a second step 14*b*, and a third step 14*c*. Corresponding to the structure of the plunger 9, a first diameter reduction portion 16*a*, a second diameter reduction portion 16b, and a third diameter reduction portion 16c are formed on an inner surface of a liquid discharge hole 15 inside the tapered tube 3 of the barrel 1, and the structure of the diameter reduction portions is formed such that a diameter thereof is reduced and an interval between the diameter reduction portions is shortened as the tapered tube 3 goes frontward, so that the tapered tube 3 may correspond and be coupled to the plunger 9.

In addition, in order to realize the reuse prevention structure, the needle hub H is fastened to a syringe protector main body 17 having a cover 18, and is assembled at a front portion thereof to a needle cap C for covering the injection needle 12.

In the above structure, in the needle hub H, the insertion groove 13 is formed inside an inner diameter portion 19 into which the tapered tube 3 of the front discharge end of the barrel 1 is inserted, so that a plunger contact surface 20 is inserted into the tapered tube 3 at the front discharge end of the barrel 1 to be brought into close contact with a reduced diameter front end surface of the plunger 9 without clearance.

Figure 5:
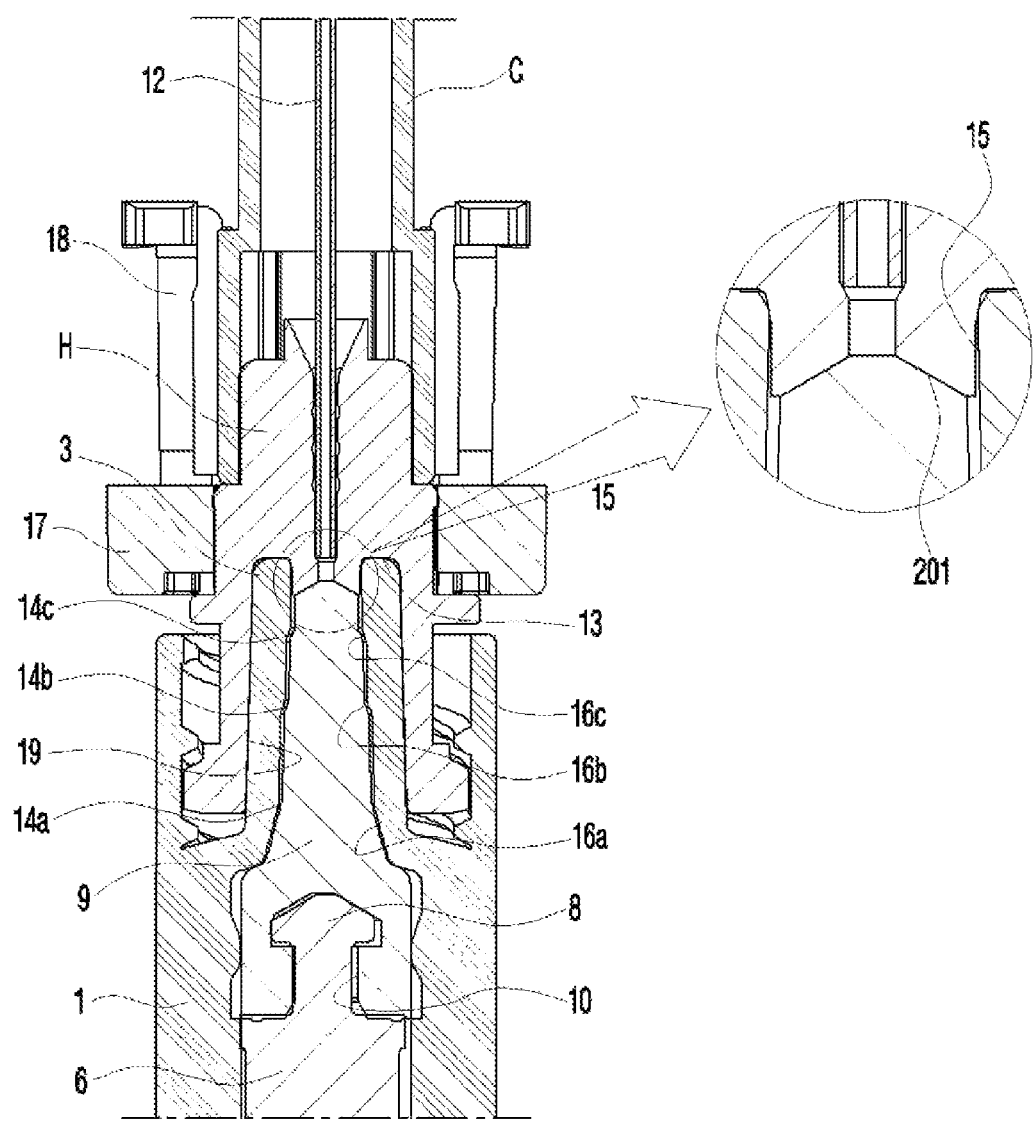
FIG. 5 is an enlarged sectional view showing a main part of the assembled syringe according to another embodiment of the present disclosure.

FIG. 5 is an enlarged sectional view showing a main part of the assembled syringe according to another embodiment of the present disclosure. The insertion groove 13 for the tapered tube of the barrel 1 is formed, and a plunger contact surface 201 configured to be inserted into the tapered tube 3 of the front discharge end of the barrel 1 is formed in a recessed "V" shape and a front end section of the plunger 9 is also formed in a shape protruding in a "V" shape corresponding to the shape of the plunger contact surface 201, so that the barrel and the needle hub are fastened to each other without clearance.

Meanwhile, needle cap fastening grooves 21 are formed along an outer circumference of the needle hub H. In the needle cap fastening grooves 21, "V"-shaped insertion guides 22 are formed in four directions at a front portions of opening of the needle cap fastening grooves 21, so that fastening protrusions 23 famed on an inner surface of the needle cap C may be unaffectedly guided and easily aligned and fastened to the needle cap fastening grooves 21.

In the syringe having the above described structure, when the injection needle 12 is injected into a separate medicinal liquid container and the plunger rod 6 is pulled as usual use of a syringe, the plunger 9 fastened to the front end of the plunger rod 6 moves rearward in the cylinder and liquid medicine is filled into the barrel 1. When the barrel 1 is filled with the liquid medicine, the plunger rod 6 is pushed while the injection needle 12 is inserted in the skin of a patient, so that the plunger 9 is moved forward along the inside of the barrel 1 to push the injection filled in the barrel to be discharged through the injection needle 12 to complete the injection. When the plunger 9 reaches an end of the barrel 1, the plunger 9 is fully inserted into the discharge hole 15 inside the tapered tube 3 of the barrel 1.

As the first step 14a, the second step 14b, and the third step 14c of the plunger 9 are brought into contact with the first diameter reduction portion 16a, the second diameter reduction portion 16b, and the third diameter reduction portion 16c formed in the discharge hole 15 inside the tapered tube 3 of the barrel 1 in order, all the remaining injection is discharged through the injection needle 12. The plunger 9 is formed in the long conical shape and has a multiple-step structure consisting of a plurality of steps in which an interval between steps is shortened as the plunger goes frontward, so that the pressure is distributed sequentially to reduce the reaction pressure applied to the plunger 9. Accordingly, the injection may be injected with smooth and constant pressure until the end of the injection without an effort, reducing pain for the patient. At the same time, in the needle hub H, the insertion groove 13 is formed inside the inner diameter portion 19 into which the tapered tube 3 of the front discharge end of the barrel 1 is inserted. Accordingly, the plunger contact surface 20 is unaffectedly inserted into the tapered tube 3 of the front discharge end of the barrel 1 to be brought into close contact with the reduced diameter front end surface of the plunger 9, so that the entire amount of injection liquid may be injected without the remaining injection liquid in the syringe.

In the needle cap fastening grooves 21 provided along the outer circumference of the needle hub H, the "V"-shaped insertion guides 22 are formed in four directions at the front portions of the openings of the needle cap fastening grooves 21, so that the fastening protrusions 23 formed on the inner surface of the needle cap C are unaffectedly guided and easily aligned and fastened to the needle cap fastening grooves 21. Therefore, even when the needle cap C is roughly aligned and fastened to the needle hub, the needle cap C may be guided by the "V"-shaped insertion guides 22 to make the fastening easily and precisely.

Although the invention is described with reference to specific items such as specific structural elements, to merely some embodiments, and to drawings, such specific details disclosed herein are merely representative for purposes of helping more comprehensive understanding of the present disclosure. The present disclosure, however, is not limited to only the example embodiments set forth herein, and those skilled in the art will appreciate that the present disclosure can be embodied in many alternate forms.

Accordingly, the present disclosure is intended to cover not only the exemplary embodiments, but also various alternatives, modifications, equivalents and other embodiments that may be included within the spirit and scope of the present disclosure as defined by the appended claims.

What is claimed is:

1. A Luer-lock fastening needle hub for a syringe which comprises a barrel comprising a finger grip at a rear end of the barrel and a Luer-lock connector at a front discharge end of the barrel, in which a thread portion is formed on an inner surface of the Luer-lock connector outside a tapered tube; a plunger rod inserted into an inside of the barrel and comprising a push end at a rear end of the plunger rod; and a plunger coupled to a front end of the plunger rod,
the needle hub being configured to be screwed and fastened to the Luer-lock connector and having an injection needle mounted to a front end of the needle hub,
the needle hub comprising an insertion groove for the tapered tube of the barrel, the insertion groove being formed on an inner diameter portion into which the tapered tube of the front discharge end of the barrel is inserted, so that a plunger contact surface of the needle hub is inserted into the tapered tube of the front discharge end of the barrel to be brought into close contact with a reduced diameter front end surface of the plunger without clearance,
wherein the plunger contact surface that is inserted into the tapered tube of the front discharge end of the barrel is formed in a recessed "V" shape, and
wherein "V"-shaped insertion guides are formed in four directions at front portions of openings of needle cap fastening grooves, wherein the needle cap fastening grooves are formed along an outer circumference of the needle hub, each of the "V"-shaped insertion guides having a radial extension portion extending from the outer circumference of the needle hub and a circumferential extension portion extending in both circumferential directions from an upper end portion of the radial extension portion so that fastening protrusions formed on an inner surface of a needle cap are unaffectedly guided by the insertion guides and easily aligned and fastened in the needle cap fastening grooves.

\* \* \* \* \*